United States Patent [19]

Eddy et al.

[11] 4,262,023

[45] Apr. 14, 1981

[54] FROZEN MULTIPLE-STRAIN CHEESE STARTER COMPOSITION

[75] Inventors: Denis I. Eddy, North Ryde; John P. Grace, Glenfield, both of Australia

[73] Assignee: Mauri Brothers & Thomson (Aust.) Pty. Limited, Sydney, Australia

[21] Appl. No.: 970,014

[22] Filed: Dec. 18, 1978

[30] Foreign Application Priority Data

Dec. 22, 1977 [AU] Australia ............................... PD2850

[51] Int. Cl.³ .................... A23C 19/02; C12N 1/04
[52] U.S. Cl. ...................................... 426/36; 426/43; 426/61; 435/260
[58] Field of Search .......................... 426/61, 36, 43; 435/260

[56] References Cited

U.S. PATENT DOCUMENTS

| Re. 28,276 | 12/1974 | Farr | 426/61 X |
| 3,344,617 | 10/1967 | Rinfret et al. | 435/260 X |

OTHER PUBLICATIONS

Baumann, et al., Freezing of Lactic Cultures, J. Da. Sci., vol. 49, 1966 (pp. 259–264) SF221J8.

*Primary Examiner*—David M. Naff
*Attorney, Agent, or Firm*—Beveridge, De Grandi, Kline & Lunsford

[57] ABSTRACT

The invention relates to cheese starter compositions comprising a plurality of discrete pellets containing frozen, live bacteria, wherein each pellet contains at least one strain of bacterium which is not appreciably present in at least one other of the pellets. In a preferred form of the invention, each pellet contains a single strain of bacterium, while in the composition as a whole there are at least two and preferably more strains.

4 Claims, 1 Drawing Figure

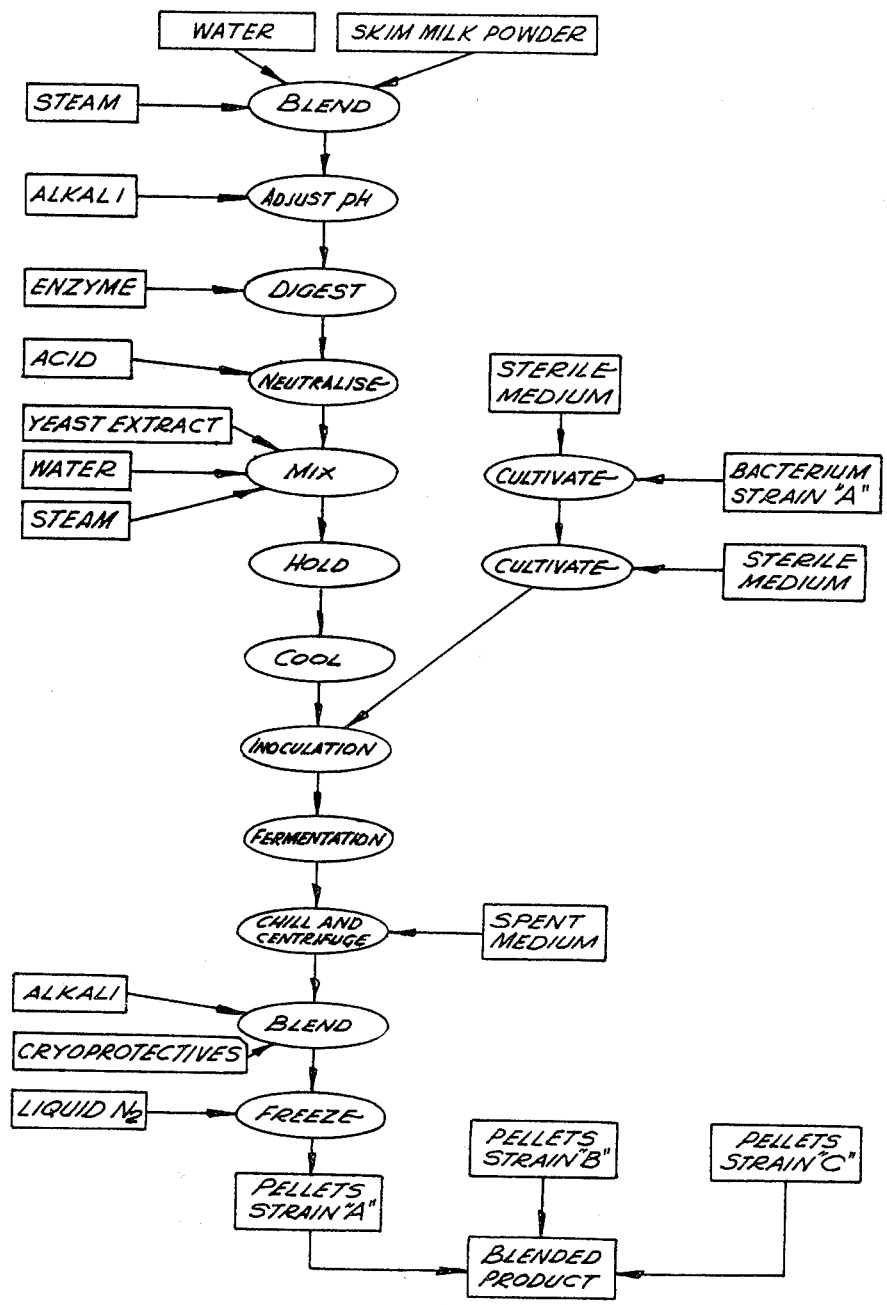

FROZEN MULTIPLE-STRAIN CHEESE STARTER COMPOSITION

FIELD OF THE INVENTION

The present invention relates to frozen, concentrated bacterial cultures for the manufacture of cheese.

BACKGROUND OF THE INVENTION

In the commercial manufacture of cheese, fermentation of the cheese milk is initiated by inoculating the cheese milk with a culture of selected bacteria. Such a culture of bacteria is known as a cheese starter.

To achieve a sufficient bacterial activity and quantity in the milk within a reasonable time, it is usual to cultivate the selected strain or strains of bacteria through several stages of increasing volume in a sterile medium such as sterilised milk to a "mother culture" stage. There follows a culture known as a "bulk starter" which forms the inoculum for the manufacturing milk. Bulk starters are usually cultivated within the cheese factory, and cannot be stored for long periods. Because the starter is transferred through several stages, the manufacture of bulk starters is not only time consuming but carries the risk of infection, not least by bacteriosphage. Another problem inherent in bulk starters is that the activity of the culture may be difficult to control with precision.

To overcome some of the problems inherent in the bulk starter method, it has been proposed to produce concentrated starters in which the bacteria have been harvested from the medium in which they were grown. Such concentrates have a sufficiently high activity that they may be added directly to the cheese vat replacing many times, typically fifty, their own volume of bulk starter. It has been proposed to manufacture such concentrated starters outside the cheese factory and away from the factory bacteriophage population, and to store them at cryogenic temperatures until required for use. The present invention relates to frozen, concentrated cheese starters.

Cheese starters may be either "single strain" cultures or "mixed" cultures. A mixed culture may not only contain several strains of the same species, but may contain several species or even several genera. The choice between a single strain culture and a mixed culture depends both on the variety of cheese being produced, and on tradition. It is principally in Australia and New Zealand that single strains have been used commercially, and even in the former country, mixed cultures have often been preferred. In the United States of America, virtually all cheese is made from mixed cultures. The commercially available mixed cultures are identified by code number, and the component strains and species are not, as a rule, characterised.

When mixed cultures are grown in standard media such as milk or whey, occasional bacteriophage infection is unavoidable. Because the susceptibility to any given bacteriophage varies widely from one microorganism or strain of micro-organism to another, the relative strength of the components can vary grossly as a result of such infection. Even in the absence of infection, the components of a mixed culture may not always attain equilibrium, and strain dominance and disturbance of proportions may occur as a result of differential growth rates, excretion of antibiotic agents, and other such effects. The relative proportions of the components are also significantly affected by changes in the composition of the medium, including seasonal changes in milk composition.

The susceptibility to bacteriophage attack can be reduced by growing the cultures in "bacteriophage inhibitory media", but strain imbalance due to other causes is found to be variably accentuated in those media.

Variations in the proportions of the various components in a mixed culture cause discernible variations in the properties of the cheese. Once a bacteriophage infection has taken place, it is extremely difficult to get rid of the offending bacteriophage from the factory environment because of the lack of characterisation of the microorganisms in the culture or available alternative mixed cultures.

By using single strain cultures, many of the disadvantages inherent in mixed cultures may be avoided. For example, if a single strain culture is attacked by a given bacteriophage, a different strain of the same species which has been characterized as having no appreciable susceptibility to the same bacteriophage may be substituted. Accordingly, to guard against the risk of bacteriophage infection, it has been proposed to employ several "phage-unrelated", single-strain cultures in rotation. Even so, bacteriophage for one strain can sometimes undergo mutation to increase its virulence towards the other strains.

The consequences of bacteriophage attack on a single-strain starter culture or in a single-strain cheese vat are much more drastic, since so many of the population can be destroyed as to lead to complete failure of acid production. Another major drawback of single-strain cultures is in the variation of the taste and texture of the product produced by different strains. Such an inconsistent product does not find favour with consumers. Furthermore, the different single strains have differing temperature susceptibilities, which means that, for optimum performance, the cheesemaking procedure needs to be varied as the strain is changed.

SUMMARY OF THE INVENTION

The present invention provides a frozen, concentrated cheese starter which shares the advantages of both mixed systems, in having more than one strain/species, and single systems, in having all components characterized, while avoiding many of the disadvantages of each type.

In one form, the present invention provides a cheese starter composition comprising a plurality of discrete pellets containing frozen, live bacteria, characterised in that each pellet contains at least one strain of bacterium which is not appreciably present in at least one other of the pellets. In a preferred form of the invention, each pellet contains a single strain of bacterium, while in the composition as a whole there are at least two and preferably more strains. It is proposed to refer to such a starter as a "multiple-strain" starter in distinction to a mixed-strain starter, which also contains two or more, but uncharacterised, strains.

The term "pellet" as used throughout this specification refers to a solid particle of any shape, and may in particular refer to cubes, spheres, flakes, or randomly-shaped particles. The pellets may be made by freezing discrete units of liquid culture or by fragmentation of a larger frozen piece. The size of the pellets may vary from the size of small grains to substantial blocks, so long as in any intended dose for cheesemaking purposes, at least two and preferably more pellets are included.

A major advantage of the cheese starter product according to the present invention is that uniformity of starter composition can be achieved simply by selecting the correct ratios of the various single strains which are required to make up the final starter product.

Another important advantage of the present invention is in the facility with which the problems of bacteriophage infection can be overcome. If such an infection occurs in a cheese factory, it is a relatively simple matter to test the bacteriophage against the various single strains making up the starter then in use, and to determine which of those strains are susceptible to that bacteriophage. A new cheese starter composition may then be blended from pellets of single strains, omitting the strain or strains which are susceptible to the phage, and possibly substituting other non-susceptible strains which compensate for the removed strain to give a cheese product of substantially identical taste and texture.

The selection of strains to be combined together is very much a matter of choice, depending on the particular characteristics desired for the cheese. Desirably, the starter should be a blend of several 'phage-unrelated' strains, to minimise the risk of total failure in the event of infection. The invention is not restricted to the selection of any particular bacterial species or strains, and the selection of the strains and derivatives will depend on the type of cheese to be manufactured. The following examples illustrate typical strain blends for some types of cheese, but it should be understood that other types of cheese can be made from cheese starters according to the invention, and the selection of species and strains may be made accordingly. In Example 1, the strains are identified according to NCDO (National Collection of Dairying Organisms, United Kingdom) deposit numbers. The strains of Examples 2 through 4 are identified according to nomenclature in general use in the United Kingdom, Ireland, Australia and New Zealand, and may be obtained from Statutory authorities in those countries, including the Commonwealth Scientific and Industrial Research Organisation, Division of Food Research, Dairy Research Laboratory, Graham Road, Highett, Victoria Australia.

EXAMPLE 1

This blend of *Streptococcus cremoris* strains or derivatives is suitable for the manufacture of a cheddar cheese.

| Species | Strain | Activity (Arbitrary Units) |
| --- | --- | --- |
| Streptococcus cremoris | 607 | 1 |
| Streptococcus cremoris | 1196 | 4 |
| Streptococcus cremoris | 1199 | 1 |

EXAMPLE 2

This blend of *Streptococcus lactis* and *Streptococcus cremoris* strains or derivatives is also suitable for the manufacture of a cheddar cheese.

| Species | Strain | Activity (Arbitrary Units) |
| --- | --- | --- |
| Streptococcus lactis | ML8 | 1 |
| Streptococcus cremoris | AM1 | 2 |
| Streptococcus cremoris | AM2 | 2 |
| Streptococcus cremoris | P2 | 1 |

EXAMPLE 3

This blend of *Streptococcus thermophilus* and *Lactobacillus helveticus* strains or derivatives is suitable for the manufacture of Italian-type cheese such as mozzarella.

| Species | Strain | Activity (Arbitrary Units) |
| --- | --- | --- |
| Streptococcus thermophilus | $TS_2$ | 1 |
| Lactobacillus helveticus | $LB_1$ | 1 |

EXAMPLE 4

This blend of *Streptococcus lactis*, *Streptococcus cremoris* and *Leuconostoc cremoris* strains or derivatives is suitable for the manufacture of Gouda and Edam type cheeses.

| Species | Strain | Activity (Arbitrary Units) |
| --- | --- | --- |
| Streptococcus lactis | ML8 | 3 |
| Streptococcus cremoris | AM1 | 6 |
| Leuconostoc cremoris | LnC* | 1 |

(*ATCC 19254 may also be used.)

Further modifications may be made to these and other blends to produce desired flavour characteristics. For example, if a buttery flavour is required, a strain of *Streptococcus diacetilactis* (such as $DRC_1$ through $DRC_3$ or ATCC 15346) may be added.

BRIEF DESCRIPTION OF THE DRAWINGS

By way of example, a process for manufacturing a cheese starter according to the present invention will be described with reference to the accompanying drawing which is a schematic flowchart illustrating a preferred method of making a cheese starter blend according to the invention.

DESCRIPTION OF THE PREFERRED EMBODIMENT

Skim milk powder (350 kg) is blended in water (5,000 liters) and heated with steam. The pH of the reconstituted skim milk is adjusted to 8.5 by the addition of alkali such as caustic soda or ammonium hydroxide. A suitable enzyme such as trypsin or papain (up to 2 kg) is added, and the milk is digested at from 40°–80° C. for 1 to 2 hours to break down the casein present in the milk to smaller peptides and some free amino acids. The medium is then neutralised to pH 7 with hydrochloric acid. A pasteurized solution of yeast extract (70 kg) in water (350 liters) at pH 7 is added to the medium. Depending on the strain of bacterium to be cultivated, it may also be desirable to add about 70 kg of lactose to the medium to supplement that present in the skim milk.

The volume of the medium is raised to 7,000 liters, and the medium is pasteurized at 85° C. for approximately half an hour before being rapidly cooled to 30° C. The pasteurisation preferably takes place under nitrogen.

A single strain (Strain "A") of a suitable bacterium such as *Streptococcus cremoris* or *Streptococcus lactis* is cultivated in 2.8 liters of a sterile medium of 3% to 10% reconstituted skim milk containing 1% yeast extract and 1% of mineral salts solution buffered with 2.36% sodium glycerophosphate.

At an inoculum density of from 5 to $10 \times 10^8$ colony forming units per ml (cfu.ml$^{-1}$), and at a pH of 5–5.5, the culture is transferred to 140 liters of a similar, buffered sterile medium in which the inoculum density grows to $2-3 \times 10^9$ cfu.ml$^{-1}$ while the pH drops to 4.5. The culture is then added to the pasteurised medium, and the medium is held at 30° C. and is agitated while fermentation takes place. Preferably, the culture is kept under a slight positive pressure of nitrogen gas, to prevent the ingress of airborne microorganisms and to preserve the anaerobic conditions. As fermentation proceeds, the pH is monitored and alkali is added to neutralise lactic acid produced by the fermentation. The preferred alkali is ammonium hydroxide, although other alkalies such as sodium hydroxide, potassium hydroxide or mixtures of these substances may be used. The optimum pH will depend on the species of bacterium. For *Streptococcus cremoris*, the preferred pH is about 6.0, while for *Streptococcus lactis*, the preferred pH is about 6.3. The fermentation is continued until acid generation (and alkali uptake) ceases, or until sufficient growth while avoiding onset of culture senescence, as judged from experience, has occurred, typically after from 6 to 10 hours.

After fermentation has ended, the temperature of the medium is rapidly chilled from 30°, to about 9° C. As soon as the temperature passes below about 25°, the bacteria are harvested by any suitable concentration device. A preferred method of harvesting is by centrifugation, for example by means of an Alfa Laval Bactofuge, model D3187M. The preferred concentration ratio is in the range of 40:1 to 60:1, yielding a viscous, creamlike material.

Sodium glycerophosphate is added to the creamlike concentrate to give a molarity of the order 0.075. The pH is then adjusted to about 6.8 by addition of caustic soda, and lactose is added to produce a final concentration of about 7.5%. Both the glycerophosphate and lactose function as cryoprotective agents.

After the addition of the cryoprotective agents, the temperature of the concentrate is reduced slowly to just above the freezing point (around −6° C.) and is then rapidly reduced to −80° C. by known means such as nitrogen vapour tunnel freezer. In a simple embodiment of the invention, the culture is frozen as a thin layer on a flat tray and is subsequently fragmented into pellets. Alternatively, the mixture can be frozen on a compartmented vessel like an iceblock tray so that it freezes in the form of discrete pellets.

The same procedure is repeated using other strains "B" and "C" of bacteria to form a stock of pellets of each other strain. Pellets of the various strains are then mixed together while frozen to produce a cheese starter product of the desired strain composition.

While it is preferred that each culture contain a single strain, some of the advantages of the invention may be achieved by fermenting different combinations of strains, to produce multiple-strain pellets, and by blending together multiple-strain pellets of different combinations to produce a total product having the desired strain combination.

The product may be stored safely for periods of up to six months at temperatures not greater than −40° C., or even longer depending on the strains used. At −110° C., storage periods of several years may be expected.

In use, the product is simply added to the vat of cheese milk with mild agitation until thawed. Typically, an amount of 1 kilogramme would be used for a volume of 1,000 gallons of cheese milk.

We claim:

1. A multiple-strain cheese starter bacteria composition consisting essentially of a plurality of discrete frozen pellets containing frozen, live bacteria, wherein the pellets as a whole contain at least two strains of cheese starter bacteria with each pellet containing (a) essentially only one strain of cheese starter bacteria, and (b) at least one cryoprotective agent.

2. A cheese starter composition according to claim 1, wherein said bacteria are selected from the genera Streptococcus, Lactobacillus and Leuconostoc.

3. A method of making a cheese wherein the bacterial fermentation of a milk-based substrate is initiated by the addition of a multiple-strain cheese starter bacteria composition consisting essentially of a plurality of discrete frozen pellets containing frozen, live bacteria, wherein the pellets as a whole contain at least two strains of cheese starter bacteria with each pellet containing (a) essentially only one strain of cheese starter bacteria, and (b) at least one cryoprotective agent.

4. A method of making a cheese according to claim 3, wherein said bacteria are selected from the genera Streptococcus, Lactobacillus and Leuconostoc.

* * * * *